United States Patent [19]

Kushida

[11] Patent Number: 4,675,529
[45] Date of Patent: Jun. 23, 1987

[54] FLUORESCENT SPECTRAL ANALYSIS APPARATUS

[75] Inventor: Takashi Kushida, Minoo, Japan

[73] Assignee: Olympus Optical Co., Ltd., Tokyo, Japan

[21] Appl. No.: 716,855

[22] Filed: Mar. 28, 1985

[30] Foreign Application Priority Data

Mar. 31, 1984 [JP] Japan ................................. 59-64496

[51] Int. Cl.$^4$ .......................................... G01N 21/64
[52] U.S. Cl. .................................... 250/458.1; 128/6; 128/665; 250/227; 356/317; 356/318
[58] Field of Search ............................. 250/458.1, 227; 356/318, 317; 128/665, 6

[56] References Cited

U.S. PATENT DOCUMENTS 4,156,809  5/1979  Phillips ................................ 455/608
4,292,537  9/1981  Davies et al. .................... 250/361 R

FOREIGN PATENT DOCUMENTS 3303510  7/1983  Fed. Rep. of Germany ... 250/458.1

OTHER PUBLICATIONS

Shuichi Kinoshita, Hironobu Ohta and Takashi Kushida, "Subnanosecond Fluorescence-Lifetime Measuring System Using Single Photon Counting Method with Mode-Locked Laser Excitation", *Rev. Sci. Instrum.* vol. 52, No. 4 (Apr. 1981), pp. 572-575.

J. H. Kinsey and D. A. Cortese, "Endoscopic System for Simultaneous Visual Examination and Electronic Detection of Fluorescence", *Rev. Sci. Instrum.* vol. 51, No. 10 (Oct. 1980), pp. 1403-1406.

*Primary Examiner*—Janice A. Howell
*Attorney, Agent, or Firm*—Frishauf, Holtz, Goodman & Woodward

[57] ABSTRACT

A fluorescent spectral analysis apparatus comprises a source of a laser beam, and first and second optical fibers to be inserted in an endoscope with forward ends extended from a distal end of the endoscope. The first optical fiber guides the laser beam emitted from the source to a subject portion to be analyzed and the second optical fiber transmits a fluorescent light generated from the subject portion due to irradiation with the laser beam. The fluorescent light is detected by a light-receiving element. The time interval between the instant of reception of the fluorescent light by the light receiver and the instant of generation of the laser beam from the source is measured.

9 Claims, 6 Drawing Figures

FIG. 1
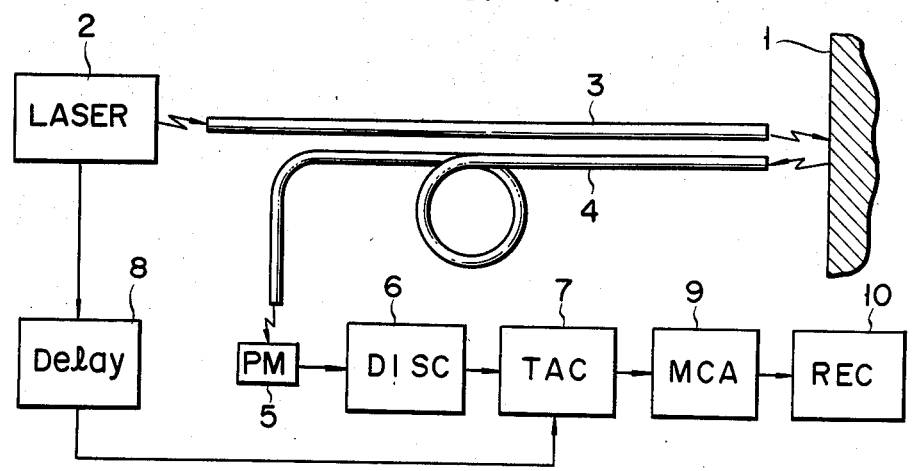
FIG. 2
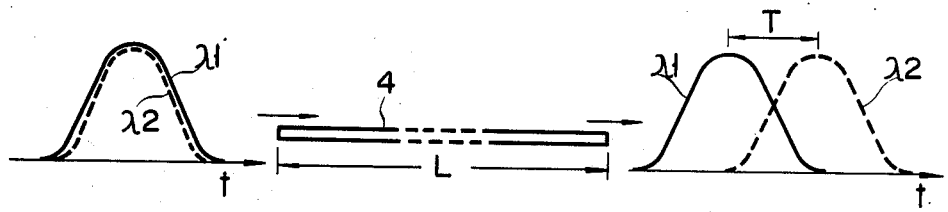
FIG. 3A    FIG. 3B    FIG. 3C
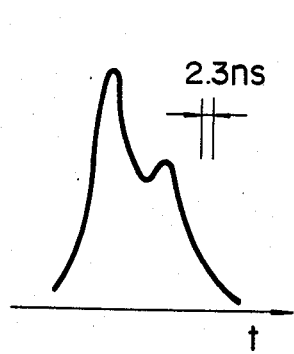 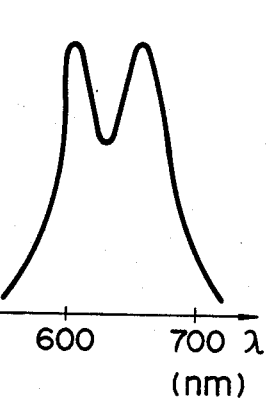 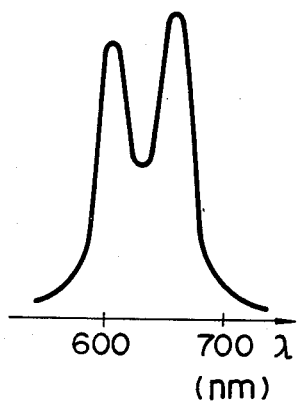

FLUORESCENT SPECTRAL ANALYSIS APPARATUS

BACKGROUND OF THE INVENTION

This invention relates to a fluorescent spectral analysis apparatus, which is simple, has high utility and permits effective fluorescent analysis of a portion of the body, for instance, by a single photon counting method.

Recently, diagnostic medical technology using lasers has been actively developed. For example, it has been a practice to cure cancer through a photochemical reaction of pigments (e.g., hematoporphyrin) selectively introduced in the cancer tissues and excited by irradiation with laser beams. Also, it has been a practice, for the purpose of diagnostic medical treatment, to make spectral analysis of cancer tissues or pigments selectively introduced therein using a laser excited fluorescent microscope or the like.

Heretofore, the spectral analysis of cancer tissues or the like using the laser-excited fluorescent microscope is carried out by irradiating the subject portion to be analyzed with exciting laser beams and coupling fluorescent light generated from the subject portion due to irradiation of the laser beams through a monochrometer to a multi-channel spectral analysis apparatus or the like. The monochrometer, however, is a large-scale optical instrument requiring precise adjustment, so that its operability and portability are very inferior. Besides, the sensitivity of the spectral analysis is low. Therefore, it is impossible to make ready fluorescent analysis of the intended portion.

SUMMARY OF THE INVENTION

An object of the present invention is to provide a fluorescent spectral analysis apparatus, which is simple in construction, has high utility and permits fluorescent analysis of the subject portion with high sensitivity and high precision.

According to the invention, fluorescent light generated from the subject portion to be analyzed by irradiation with pulse light is transmitted through an optical fiber and is detected, and the time interval between the instant of reception of the fluorescent light and the instant of generation of pulse light for irradiation of the subject portion is measured to effect the fluorescent analysis. High-repetition rate short-pulse light having an intensity such that at most one photon of fluorescent pulse light is received when the subject portion is irradiated with a single pulse of light is used. Particularly, a comparatively long optical fiber is used to transmit the fluorescent pulse light for the fluorescent analysis.

According to the invention, since at most only a single photon of fluorescent pulse light is detected when the subject portion is irradiated with a single excitation light pulse and the propagation time of the fluorescent pulse light through the optical fiber varies with the wavelength components of the light, the wavelength of the received and detected fluorescent pulse light can be determined by measuring the propagation time. By using high-repetition rate short-pulse light and repeatedly executing the detection of the fluorescent pulse light, the fluorescent spectral analysis of the subject portion can be effected with high sensitivity and high precision. Further, since the optical fiber is used effectively for the spectral analysis of the fluorescent light from the subject portion, there is no need to use a large-scale monochrometer, and it is possible to provide an analysis apparatus which has a simplified construction and a reduced size.

BRIEF DESCRIPTION OF THE DRAWINGS

FIG. 1 is a schematic representation of an embodiment of the invention;

FIG. 2 is a view for explaining a fluorescent light transmission characteristic of an optical fiber;

FIGS. 3A to 3C are views showing results of fluorescent analysis; and

PREFERRED EMBODIMENT OF THE INVENTION

Figure 4:
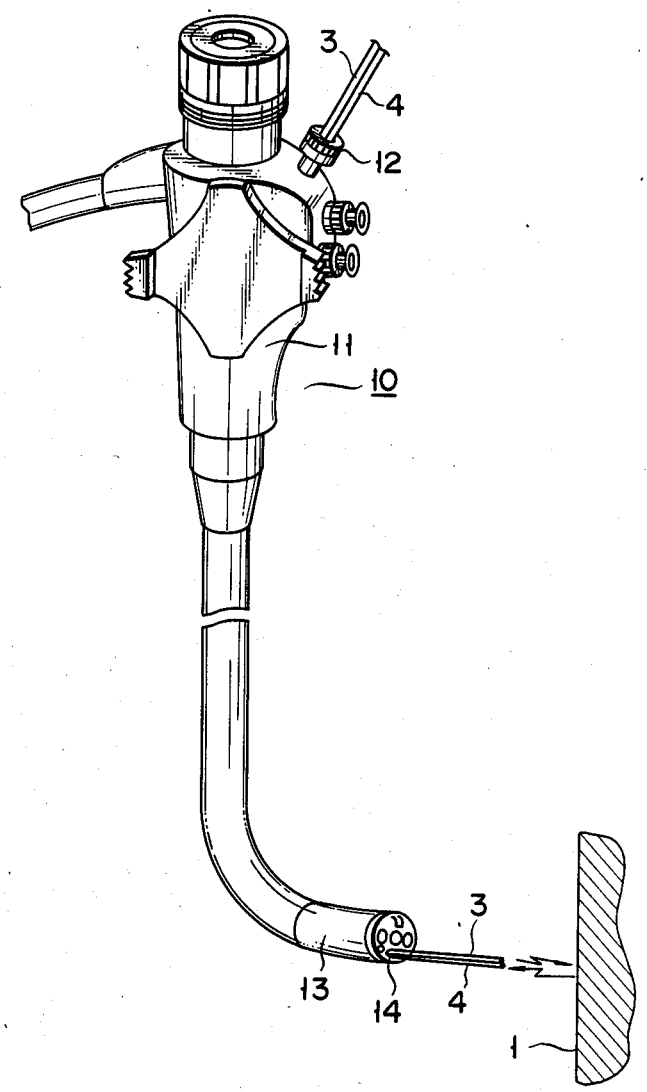
FIG. 4 is a perspective view showing a combination of the embodiment of the apparatus and an endoscope.

Now, a preferred embodiment of the invention will be described with reference to the drawings.

FIG. 1 schematically shows an embodiment of the apparatus. Reference numeral 1 designates a portion as a subject of analysis. A laser oscillator 2 generates high-repetition frequency pulse light or beam, for instance with a repetition frequency of several tens MHz and a pulse width of several psec., as excitation light for exciting the subject portion 1. The pulse light is led through a first optical fiber 3 to be projected onto the subject portion 1. When irradiated by the laser pulse light, the subject portion 1 is excited to generate fluorescent pulse light having a wavelength corresponding to its physical nature. The fluorescent pulse light is led to a second optical fiber 4, which is a low-loss optical fiber with a length of 1,000 m, for instance. The second optical fiber 4 transmits the incident pulse light to a light-receiving unit 5. The light-receiving unit 5 is a photoelectron multiplier or the like having a high speed and highly sensitive light-receiving characteristic, and it converts the incident pulse light into an electric signal.

The electric signal obtained through conversion of the fluorescent pulse light by the light-receiving unit 5, is fed to a constant fraction discriminator 6, which removes pulse components of the input signal due to a dark current in the light-receiving element 5, and noise. The output of the discriminator 6 is fed to a time peak converter 7 for obtaining the time interval between the instant of projection of the pulse light onto the subject portion 1 and the instant of incidence of the fluorescent pulse light on the light-receiving element 5. The time peak converter 7 receives an operation signal (reference signal) from the laser oscillator 2 which is received through a delay line 8, and the discriminated fluorescent pulse light signal and obtains a peak signal corresponding to the time difference between the two input signals. More specifically, the time peak converter 7 integrates a constant current in response to the discriminated fluorescent pulse signal as a start pulse and stops the integrating operation in response to the reference signal as a stop pulse, thereby obtaining the time interval as the corresponding integral value. The time interval noted above is properly measured with the pulse light projection timing represented by the reference signal as start pulse and the timing of detection of the fluorescent pulse light as a stop pulse. In the instant case, however, the projection of pulse light is done at a high rate and periodically, and the light-receiving element 5 detects only a single photon of the fluorescent pulse light as will be described later. For these reasons, the measurement of the time interval is carried out utilizing the reference signal when and only when a photon is detected by the light-receiving element 5.

The time interval data output of the time peak converter 7 is fed to a multi-channel pulse peak analyzer 9 for conversion to data representing the wavelength of the fluorescent light. The output of the analyzer 9 is fed to and recorded in a recorder 10.

The laser oscillator 2 is constructed such that it repeatedly generates, at a high rate, pulse light of such intensity that when one light pulse is incident on the subject portion 1, less than one fluorescent light pulse (i.e., photon) is detected by the light-receiving unit 5 as fluorescent light generated by the subject portion 1 and incident on the unit 5 through the second optical fiber 4. This permits analysis of the fluorescent pulse light due to pulse light incident on the subject portion 1 using a single photon counting process. The laser oscillator 2 which can generate the pulse light as noted above may be a CW mode synchronous laser (e.g., an argon laser or a pigment laser) which can generate a short light pulse series with a pulse width of 200 psec., and a pulse repetition frequency of 80 MHz.

The second optical fiber 4 is a low-loss fiber, e.g., a quartz fiber of graded index type. Its length is greater than a length satisfying a relation where $\tau$ is the life (or time width) of the fluorescent light pulse and $\Delta T$ is the wavelength time difference when the fluorescent light pulse propagates through it and is less than the length through which the fluorescent light pulse is attenuated so that it can no longer be detected.

The second optical fiber 4 can transmit fluorescent light covering a wide spectral range as shown in FIG. 2. However, the propagation time varies with the wavelength $\nu$ of the transmitted light. Accordingly, if the fluorescent high pulse is transmitted through the second optical fiber 4, which has a certain length L, the time from the generation of fluorescent light from the subject portion 1 in response to pulse light incident thereon till the detection of that fluorescent light by the light-receiving element 5 after having been transmitted through the second optical fiber 4 varies greatly with the wavelength component. This means that the length of the second optical fiber 4 should be a length such that the time difference $\Delta T$ is longer than the time width of the fluorescent light pulse, and which permits time-wise separation and observation of wavelength components of the fluorescent light. Actually, however, extremely increasing the length of the optical fiber 4 gives rise to a problem in the transmission loss of the fluorescent pulse light transmitted through the optical fiber 4. The length of the second optical fiber 4 thus has to be determined appropriately so that there arises no problem in the transmission loss. An example of the length of the optical fiber 4 used for the embodiment of the apparatus is no less than 100 m and no greater than 10,000 m. Shorter optical fibers than the range noted above may be used in such case as when separating only two peaks of fluorescent light and measuring the relative intensity thereof. On the other hand, longer optical fibers than the range noted above may be used in such case as when analyzing only a longwave spectral range of the optical fiber subject to low loss in detail.

Unlike the second optical fiber 4, the first optical fiber 3 should be short so that the pulse light propagation time through it is ignorable. Where the propagation time of the pulse light through the first optical fiber 3 can not be ignored, it can be compensated for by the delay line 8. More specifically, while the delay line 8 is used to make up for the timing of generation of the reference signal which is used as stop pulse for the time measurement with respect to the fluorescent pulse light noted above, the time compensation with respect to the projected pulse light may also be done through this delay line 9.

FIGS. 3A to 3C show results of analysis of fluorescent light. More specifically, FIG. 3A shows the distribution of fluorescent light pulse detection time when hematoporphyrin (with fluorescent time of 2.3 nsec.) dissolved in dioxane is analyzed as the sample (i.e., subject material) with the apparatus according to the invention. In this analysis, a 1,000-m long optical fiber is used as the second optical fiber 4. FIG. 3B shows the result of wavelength conversion of this time distribution through the time peak converter 7 and multi-channel pulse peak analyzer 9. FIG. 3C shows the result of spectral analysis of the same sample material with a prior art spectral analyzer. As is obvious from the comparison of the graphs of FIGS. 3B and 3C, with the apparatus according to the invention it is possible to obtain spectral analysis results which are comparable with analysis results obtainable with the prior art large-scale apparatus.

As has been shown, with the fluorescent spectral analysis apparatus according to the invention, it is possible to effectively obtain the fluorescent spectrum of the subject portion 1 by irradiating the portion 1 with short pulse light repeatedly generated at a high rate and obtaining the light detection time distribution of the fluorescent pulse light generated from the subject portion 1 as a result of the irradiation thereof with the pulse light by receiving the fluorescent pulse light by a single-photon counting method through the second optical fiber 4. In addition, the spectral analysis can be made without a large-scale spectral analyzer and the apparatus according to the invention can be greatly simplified in construction and reduced in size. Further, the apparatus can be handled more easily. Further, since the spectral analysis is performed using short pulse light repeatedly generated at up to several tens MHz and repeatedly detecting the fluorescent pulse light, the measurement can be done in a short period of time, with high precision and with high sensitivity.

A use of the fluorescent spectral analysis apparatus according to the invention in combination with an endoscope for observing gastric cancer tissues in man will now be described with reference to FIG. 4. The first and second optical fibers 3 and 4 are inserted through a forcep inserting opening 12 of a control section 13 of an endoscope 10 inserted into the body. The ends of the fibers 3 and 4 are extended from forcep drawing opening 14 at the distal end 13 to the vicinity of the subject portion to be analyzed. In this state, exciting laser light is led through the first optical fiber 3 to irradiate the subject portion 1. Fluorescent light that is generated from the subject portion 1 as a result of irradiation with the laser light, is led through the second optical fiber 4 to a light receiving unit 5 which is provided outside the body. The first and second optical fibers need not be introduced with the same forcep channel into the body. For example, they may be introduced with different forcep channel. Alternately, at least one of them may be assembled in the other parts or members of the endoscope such as a light guide for illumination or image bundle. Where using a light guide as a first optical fiber 3, a suitable changing member is provided to selectively guide the laser beam and illumination light into the light guide. Also where the second optical fiber is inserted through an image bundle, the end of the second optical fiber is extended from the image bundle at the control section. With the above arrangement, a desired portion may be irradiated with laser light while observing it with the endoscope. It is thus possible to obtain fluorescent pulse light generated from an affected part which is intended to be analyzed. In this case, the measurement is completed simultaneously over the entire wavelength range and in as short measurement time as several seconds. Thus, a movement of the subject portion due to such cause as respiration of the patient can be ignored, so that it is possible to obtain precise analysis free from measurement errors. Further, the fluorescent analysis of the affected part can be obtained by merely inserting the optical fibers through the forcep inserting opening while observing it with the endoscope and without inserting the apparatus into the body. Thus, the measurement can be done without giving pain to the patient. Further, the apparatus is simple in construction and can be easily handled. Thus, the apparatus can greatly contribute to diagnostic medicine. Meanwhile, the lifetime of the detected fluorescent light can be simultaneously measured using a third optical fiber. More specifically, a third optical fiber which is sufficiently short unlike the second optical fiber may be inserted through the forcep inserting opening, and the lifetime of the fluorescent light may be measured by comparison of the instant when the fluorescent light is received through the third optical fiber and the instant when the fluorescent light is received through the second optical fiber 4. Further, in lieu of using the third optical fiber, the fluorescent pulse light may be spectrally detected at an intermediate point of the second optical fiber 4 for the measurement of the lifetime of the fluorescent light. Doing so permits greater effects to be expected in diagnostic medicine through observation of the internal part of the body in the spectral analysis thereof.

While an embodiment of the invention applied to a fluorescent spectral analysis apparatus has been described above, it is by no means limited to this. For example, the pulse light from the laser oscillator 2 can be directly projected onto the subject portion 1 without agency of the first optical fiber 3. Further, the pulse width of the exciting pulse light and repetition frequency thereof may be determined depending on the specification of the apparatus. Further, while the use of the fluorescent spectral analysis apparatus has been described in connection with the internal part of the body, the apparatus according to the invention can also be used for the analysis of the face skin and measurement of fluorescent light in a remote place such as an atomic reactor, mining place, etc. Further, it can be used in combination with an industrial fiber scope or the like.

What is claimed is:

1. A fluorescent spectral analysis apparatus comprising:
   a light irradiating means for irradiating a subject portion to be analyzed with a pulse light;
   an optical fiber for transmitting a pulse of fluorescent light generated from said subject portion due to irradiation with the pulse light, wherein said optical fiber has a length sufficient to produce necessary differences of the propagation time of the fluorescent light pulse through said optical fiber for different wavelength components of a spectral analysis;
   a light receiver for receiving and detecting the fluorescent light pulse transmitted through said optical fiber; and
   means for measuring the time interval between the instant of reception of the fluorescent light pulse by said light receiver and the instant of generation of the pulse light from said light irradiating means.

2. The fluorescent spectral analysis apparatus according to claim 1, wherein said light irradiating means generates a high repetition-rate, short-pulse light having an intensity such that said light receiver receives a single photon of fluorescent pulse light at most when said subject portion is irradiated with a single pulse of light.

3. The fluorescent spectral analysis apparatus according to claim 2, wherein said light irradiating means includes a coherent light source for emitting coherent pulse light and guiding member for guiding coherent pulse light to the subject portion.

4. The fluorescent spectral analysis apparatus according to claim 3, wherein said guiding member includes an optical fiber.

5. The fluorescent spectral analysis apparatus according to claim 1, wherein said optical fiber has a length of 100 m to 10,000 m.

6. The fluorescent spectral analysis of claim 1, wherein said time interval measuring means comprises a time peak converter for intergrating a constant current in response to the light from said receiver pulse as a start pulse and for stopping the integrating operation in response to the pulse light from the light irradiating means as a stop pulse, to obtain the time interval as the corresponding integral value.

7. The apparatus of claim 1, wherein $\uparrow$ is the time width of said pulse fluorescent light, and $\Delta T$ is the time required for the pulse of fluorescent light to traverse the length of said optical fiber, the length of said optical fiber being such that for all anticipated wavelengths of the fluorescent light $\Delta T > \uparrow$.

8. A fluorescent spectral analysis apparatus comprising;
   an endoscope having a control section and a distal end;
   a coherent light source for emitting coherent pulse light;
   a first optical fiber inserted in the endoscope with one end extended from the distal end, which guides the coherent pulse light to a subject portion to be analyzed;
   a second optical fiber inserted in the endoscope with one end extended from the distal end, which transmits a pulse of fluorescent light generated from said subject portion due to irradiation with the coherent pulse light, wherein said second optical fiber has a length sufficient to produce necessary differences of the propagation time of the fluorescent light pulse through said second optical fiber for different wavelength components of a spectral analysis;
   a light receiver for receiving and detecting said fluorescent light pulse transmitted through said second optical fiber; and
   means for measuring the time interval between the instant of reception of said fluorescent light pulse by said light receiver and the instant of generation of said pulse light from said light source.

9. The apparatus of claim 8, wherein $\uparrow$ is the time width of said pulse fluorescent light, and $\Delta T$ is the time required for the pulse of fluorescent light to traverse the length of said optical fiber, the length of said optical fiber being such that for all anticipated wavelengths of the fluorescent light $\Delta T > \uparrow$.

* * * * *